US006768298B2

(12) United States Patent
Katragadda et al.

(10) Patent No.: US 6,768,298 B2
(45) Date of Patent: Jul. 27, 2004

(54) TRANSVERSE CRACK DETECTION IN RAIL HEAD USING LOW FREQUENCY EDDY CURRENTS

(75) Inventors: Gopichand Katragadda, San Antonio, TX (US); Douglas Earnest, San Antonio, TX (US); Gregory Anthony Garcia, Pueblo, CO (US); Richard Paul Reiff, Pueblo, CO (US)

(73) Assignee: Transportation Technology Center, Inc., Pueblo, CO (US)

( * ) Notice: Subject to any disclaimer, the term of this patent is extended or adjusted under 35 U.S.C. 154(b) by 0 days.

(21) Appl. No.: 09/907,249

(22) Filed: Jul. 17, 2001

(65) Prior Publication Data

US 2003/0020469 A1 Jan. 30, 2003

(51) Int. Cl.[7] .......................... B61K 9/10; G01N 27/82

(52) U.S. Cl. ....................................................... 324/217

(58) Field of Search ................................ 324/217, 218, 324/225, 226, 232, 262, 263, 260

(56) References Cited

U.S. PATENT DOCUMENTS

| 2,049,764 A | * | 8/1936 | Drake | ......................... 324/260 |
| 2,884,592 A | * | 4/1959 | Wilson | ......................... 324/217 |
| 3,952,315 A | | 4/1976 | Cecco | |
| 4,510,447 A | * | 4/1985 | Moyer | ......................... 324/225 |
| 4,631,688 A | | 12/1986 | Boehm et al. | |
| 4,932,618 A | | 6/1990 | Davenport et al. | |
| 5,429,329 A | | 7/1995 | Wallace et al. | |
| 5,446,382 A | | 8/1995 | Flora | |
| 5,751,144 A | | 5/1998 | Weischedel | |
| 5,786,750 A | | 7/1998 | Cooper | |
| 6,102,340 A | | 8/2000 | Peek et al. | |

OTHER PUBLICATIONS

ZETEC, Inc., MIZ–22 Dual–Frequency Eddy Current Instrument, 1993, 1 page (front of page).
ZETEC, Inc., MIZ–22 Dual–Frequency Eddy Current Instrument, 1993, 1 page (back of page).
Zarembski et al., TTCI, Technology Digest, Review of Rail–Testing Practices and Technologies—Overseas, Jun. 1998, 4 pages.
Garcia and Reiff, TTCI, Test and Evaluation of Rail Defect Detection Technologies, Sep. 1998, 17 pages.
Reiff and Garcia, TTCI, Increasing Cost Effectiveness of Continuous Welded Rail Through Improved Rail Defect Inspection, Oct. 19, 1998, 13 pages.
Garcia and Reiff, TTCI, Technology Digest, Rail–Defect Test Facility: A Tool of Evaluating Defect–Detection Technologies, Jan. 1999, 4 pages.
Stone et al., TTCI, Rail and Wheel Inspection Systems, Pueblo, CO, Jan. 6, 1999, 9 pages.

(List continued on next page.)

Primary Examiner—Jay Patidar
(74) Attorney, Agent, or Firm—Dorr, Carson, Sloan, Birney & Kramer, P.C.

(57) ABSTRACT

A method and system for detecting transverse cracks beneath horizontal cracks in the rail way track. As a transporter moves over rail, a saturation magnetic field is generated into and across the rail head using a toroidal-shaped DC saturation magnet located a predetermined distance above the rail head. Any transverse cracks in the rail head are detected with a low frequency eddy current probe mounted centrally between the opposing pole ends of the DC magnet and over the rail head. A force is applied to the low frequency eddy current probe to hold the probe towards the rail head as the transporter moves on the rail so as to follow the wear pattern of the rail head and to minimize lift-off. A second sensor is used to sense the presence of non-relevant indications that falsely indicate possible transverse cracks by the low frequency eddy current probe.

18 Claims, 8 Drawing Sheets

OTHER PUBLICATIONS

Garcia and Reiff, TTCI, Technology Digest, Benchmarking Results of North American Rail–Flaw Detection Technologies, Feb. 1999, 4 pages.

Earnest et al., Transverse Crack Detection in Rail Heads, Proceedings of: 6th NDE Topical Conference Apr. 19–22, 1999, San Antonio, Texas, 8 pages.

Transverse Crack Detection in Railroad Rails, 18 pages of presentation material given at the Proceedings of the 6th NDE Topical Conference, Apr. 19–22, 1999, San Antonio, Texas by Douglas R. Earnest.

* cited by examiner

TRANSVERSE CRACK DETECTION IN RAIL HEAD USING LOW FREQUENCY EDDY CURRENTS

BACKGROUND OF THE INVENTION

1. Field of the Invention

The present invention relates to the detection of transverse cracking in rail heads and, more particularly, to using a low frequency eddy current system designed to detect transverse cracks in rail heads.

2. Statement of the Problem

It has been reported that 40% of rail failures are due to the occurrence of transverse cracking in the rail head. An important goal in the railroad industry is to detect such transverse cracks before such failure occurs. A transverse crack is a progressive transverse fracture occurring in the head of the rail and propagating under cyclic fatigue.

One conventional nondestructive approach for detecting transverse cracking is the use of conventional ultrasonic methods involving roller search units and contact transducers. The problem with such conventional ultrasonic approaches is that transverse cracks often occur under horizontal cracks (shelling/air gaps) which reflect ultrasound thereby masking the transverse crack. Horizontal cracking is a condition in which the cold worked layer of material above the transverse crack separates and flows over the remaining rail. This "shelling" of the rail head is a condition of the contact fatigue generated due to wheel/rail interaction.

A need exists to detect transverse cracks beneath horizontal cracks before the transverse crack grows or fails in service.

In Earnest, Katragadda, Si, and Garcia, "Transverse Crack Detection in Railroad Heads," Oral Presentation at the 6$^{th}$ NDE Topical Conference, Apr. 19–22, 1999, San Antonio, Tex., initial results were disclosed of an experimental low frequency eddy current approach designed to detect transverse cracks in rail heads. While this presentation reported results from static (stationary) testing, it did verify the ability to detect transverse cracks under horizontal cracks in rail head. Horizontal cracks are parallel to the direction of the saturated magnetic field making the probe relatively insensitive to the horizontal cracks and sensitive to any underlying transverse cracks. The static tests not only were able to detect transverse cracks under horizontal cracks, but were able to provide output signals indicating the approximate size of the transverse crack. It was further observed that higher frequencies for the eddy current did not penetrate well into the rail head whereas lower frequencies of 70 to 100 hertz provided deeper penetration. The Earnest et al. presentation speculated that the static feasibility test observed could be implemented into a push cart wherein brushes could be added to the saturating magnetic poles to increase the contact with the rail head.

A need exists to provide a low frequency eddy current system that moves along the rail at a velocity sufficient to detect transverse cracks in rail heads of actual rail tracks, that provides an eddy current probe for such moving inspections, that follows a rail head having a wear profile, that minimizes any lift-off of the probe while moving, and that couples the magnetic saturation to the rail.

A need exists also to reject those signals from the low frequency eddy current probe that are sensed to be transverse cracks, but are from non-relevant indications such as from thermite welds, plant welds, rail end joints, etc.

SUMMARY OF THE INVENTION

The present invention solves the aforestated problems by providing a novel method and system for increasing the detection of transverse cracks beneath horizontal cracks in the rail. The novel method and system of the present invention provides a low frequency eddy current system that moves along the rail at a velocity sufficient to detect transverse cracks in rail heads, that provides a low frequency eddy current probe for such moving inspections, that follows the wear profile of the rail head, that minimizes any lift-off of the probe while moving, and that couples the saturation magnet to the rail. The novel method and system of the present invention also utilizes a separate sensor such as a Hall element sensor to distinguish the low frequency eddy current signals, obtained from a transverse crack, from non-relevant indications such as thermite welds, plant welds, rail end joints, etc.

The novel method of the present invention provides moving a transporter on the rail at a velocity, generating a saturation magnetic field into and across the rail head using a DC saturation magnet mounted to the transporter a predetermined distance above the rail head, inductively coupling the opposing pole ends of the DC saturation magnet with the rail head, detecting transverse cracks in the rail head with a low frequency eddy current probe mounted centrally between the opposing pole ends of the DC saturation magnet and over the rail head, applying a force on the low frequency eddy current probe against the rail head as the transporter moves on the rail at the velocity so as to follow the wear pattern of the rail head, and to control the lift-off of the probe from the rail head.

The novel system of the present invention uses a transporter that moves along the track. A toroidal-shaped DC magnet mounted to the transporter with its opposing ends inwardly directed towards each other and aligned over the rail head to increase saturation. An inductive coupling provided between each of the poles and the rail heads increases magnetic saturation of the rail head. A low frequency eddy current probe centrally located between the poles of the toroidal-shaped DC magnet senses the presence of transverse cracks in the rail head. A carriage mounted to the transporter forces the low frequency eddy current probe towards the rail head at the central location. Protective material on the probe abuts the rail head as the transporter moves thereby protecting the low frequency eddy current probe from damage while permitting the probe to follow the wear profile. At least one wheel located on the carriage engages the rail head for controlling lift-off of the low frequency eddy current probe from the rail head.

DETAILED DESCRIPTION OF THE INVENTION

Figures 1, 2:
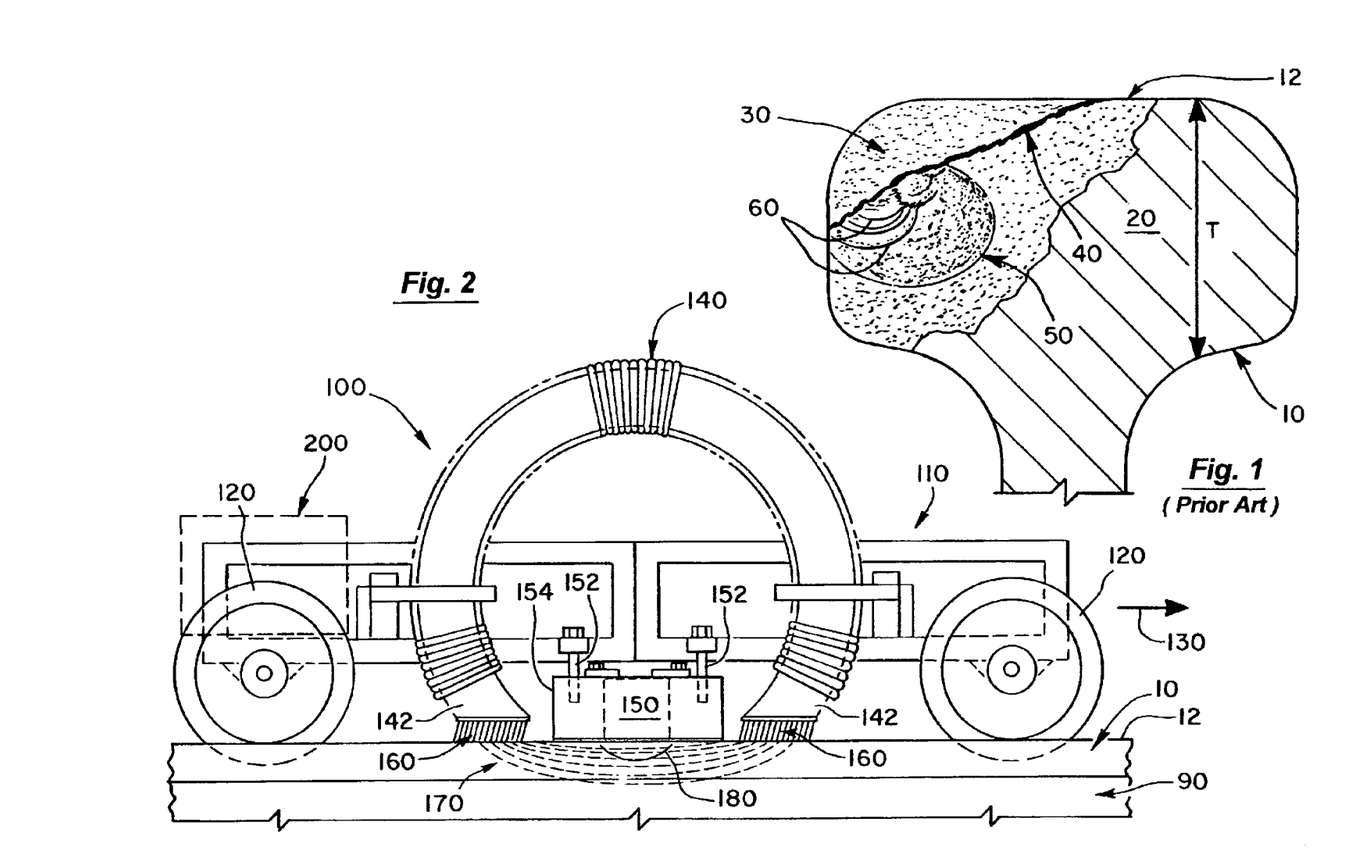
FIG. 1 is a prior art illustration of a rail head cross section showing a horizontal crack and a transverse crack lying underneath.
FIG. 2 is a side view illustration of the transporter of the present invention carrying a saturation magnet and the low frequency eddy current probe of the present invention.

1. Overview. In FIG. 1, a prior art rail head cross section 20 is shown. The rail head 10 thickness T is typically about 1.5 inches. An area of shelling 30 is shown to have a horizontal crack 40. Under the horizontal crack (shelling/air gaps) 40 is a transverse crack 50 which is typically formed in a kidney shaped pattern. The transverse crack 50 is a defect that grows in spurts sometimes resulting in concentric growth rings 60. The transverse crack 50 reaches a certain dimension and the remaining rail undergoes brittle failure.

In FIG. 2, the system 100 of the present invention is shown on rail 90. The system 100 is mounted to a transporter 110 having conventional rail wheels 120. The transporter 110 moves in the direction 130 powered in any of a number of conventional approaches. In FIG. 2, the transporter 110 is shown as a cart on rail 90 which is moved along the rail 90 at a velocity, V. Shown, by dotted lines, is a conventional means 200 for moving the transporter 110. Such conventional means 200 includes a motor of any type, a coupling of any type for pushing or pulling the transporter 110, a manually operated power source of any type, or any functional device that provides movement at velocity V in direction 130. The term "transporter" is used to mean any structural means 110 for transporting the DC saturation magnet 140 and probe carriage 100. This structural transporting means 110 includes a separate cart, as shown; incorporation into a vehicle such as a modified pick-up capable of traveling on the rail or on a road; incorporation into a train car; or incorporation into any suitable device for conveying the magnet 140 and the probe 150 along the track 90.

The low frequency eddy current system 100 uses a toroidal-shaped DC saturation magnet 140 and a low frequency eddy current probe 150 in a carriage 154. Brushes 160 are mounted at the pole ends 142 of the saturation magnet 140. Brushes 160 provide an inductive coupling between the pole ends 142 and the rail head 10. The probe carriage 154 is mounted to the cart 110 between the pole ends 142 with support hangers 152. The probe 150 abuts the upper surface 12 of the rail head 10 to maintain contact with the upper surface 12. The saturation magnet 140 is mounted to the transporter 110 with aluminum supports so as not to interfere with the saturation fields.

In operation, the DC saturation magnet 140 provides a saturated magnetic field 170 in the rail head 10. The DC saturation magnet 140 has two purposes: first, to reduce the skin effect for the low frequency eddy current probe 150 by reducing the effective rail head material permeability and; second, to eliminate signal variations due to random variations of permeability in the rail head material.

The probe 150, as will be discussed, induces a current 180 in the rail head 10. Eddy currents are alternating electrical currents which are induced in the rail head by the probe 150. The induced flow pattern is disturbed by the presence of a transverse crack 50. The disturbance in the flow pattern in turn affects the associated magnetic field which is detected.

Figure 3:
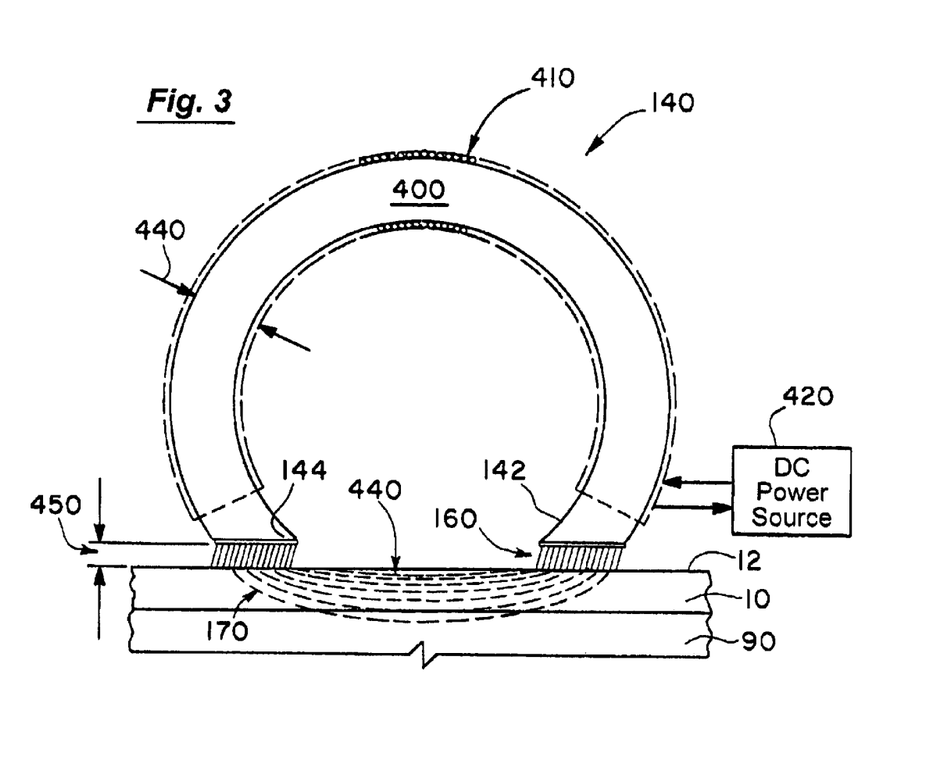
FIG. 3 sets forth the details of the toroidal-shaped DC saturation magnet of the present invention.
Figure 4:
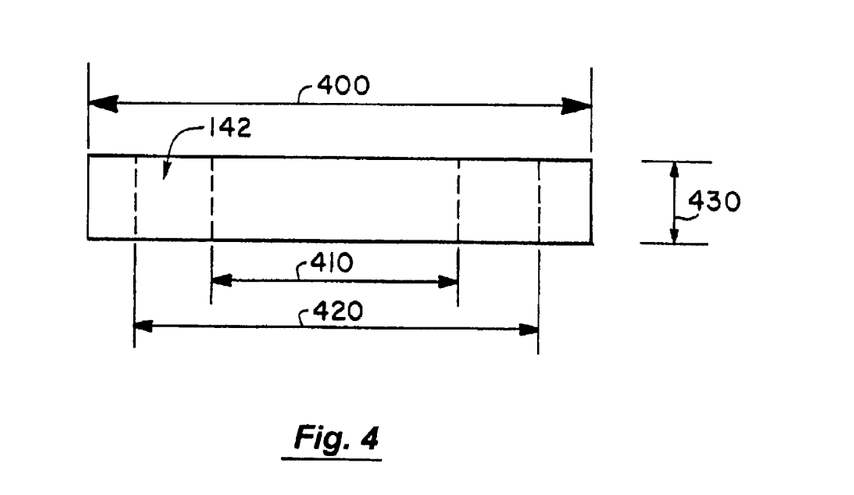
FIG. 4 sets forth the dimensions of the toroidal-shaped DC saturation magnet of FIG. 3.

2. DC Saturation Magnet. In FIG. 2, the DC saturation magnet 140 is shown to be toroidal in shape. In FIGS. 3 and 4, the details of the toroidal-shaped saturation magnet 140 are shown. In this embodiment, the saturation magnet 140 has a toroidal-shaped core 400 formed of 11 mil laminated silicone iron layers which are glued together. The material is in this embodiment EL-COR No. T0803-009 or comparable material. The dimensions for the magnet 140 of FIG. 3 are shown in FIG. 4 are set forth in Table I:

TABLE I

| Reference | Dimension (inches) | Min. (inches) | Max. (inches) |
|---|---|---|---|
| 400 | 24.00 | 23.875 | 24.125 |
| 410 | 12.00 | 11.813 | 12.187 |
| 420 | 18.00 | 17.938 | 18.25 |
| 430 | 3.00 | 3.00 | 3.031 |
| 440 | 3.00 | 2.969 | 3.031 |

In FIG. 3, layers of spiral windings 410 are shown. In the preferred embodiment, four layers of windings 410 are provided for a total of 1,082 turns. Ten gauge solid enamel wire is used. It was observed for this embodiment that approximately 1,000 turns is optimal. More turns caused heat to build up and less turns reduced the saturation effect.

The saturation magnet 410 is powered by a DC power source 420 which in the above embodiment provides 20 amps into the turns 410 in a voltage range of 40–50 volts DC. The pole ends 142 of the saturation magnet 140 are spaced 450 from the top surface 12 on the rail head 10, in this embodiment, in a range of about 0.5 to 0.75 inches. The brushes 160 are longer than the spacing 450 and each brush 160 contains 5 mil diameter carbon steel bristles.

In FIG. 2, the brushes 160 structurally function as a means 160 affixed to the opposing pole ends 142 for inductively coupling the DC saturation magnetic field 170 with the rail head 10. The inductive coupling allows for slide ability over the rail head 10. It is to be understood any suitable design or structure for performing this function could be utilized under the teachings contained herein. The brushes 160 also act to clean the surface 12 of the rail head 10 to remove dust or grease before the probe 150 slides over.

In contrast to the rectangular design used in the static test of the aforesaid Earnest presentation, the toroidal shape for the DC saturation magnet 140 of the present invention provides greater magnetic density 440 in the rail head 10 near the surface 12. The intensity of the field 170 lessens downwardly into the rail 10. The toroidal shape provides a greater cross-section of its core 400 in contact with the rail head 10. The windings 410 shown in FIG. 3 are more evenly distributed over the core and a smaller distance is provided between the pole ends.

The high intensity field 440 near the surface 12 reduces the skin-effect for the probe 150 and minimizes signal variations in probe 150 due to the rail head material. In comparison to the Earnest presentation, the toroidal-shaped saturation magnet 140 of the present invention provides a much higher intensity field 440 to eliminate manufacturing effects and material history effects that would vary the permeability of or near the surface 12 such as the horizontal cracks 40 previously discussed. As shown in FIG. 3, the opposing pole ends 142 terminate in an acute angle 144. It is to be understood that in FIG. 3, the spacing 450 is exaggerated to illustrate the effect of the brushes 160. This concentration of the magnetic saturating field 440 represents an improvement over the Earnest presentation which only disclosed the use of a set of opposing poles oriented vertical to the rail head 10. The greater intensity 440 obtained with the acute angles 144 of a toroidal-shaped magnet 400 provide greater saturation to obtain the above two stated goals.

Figure 5:
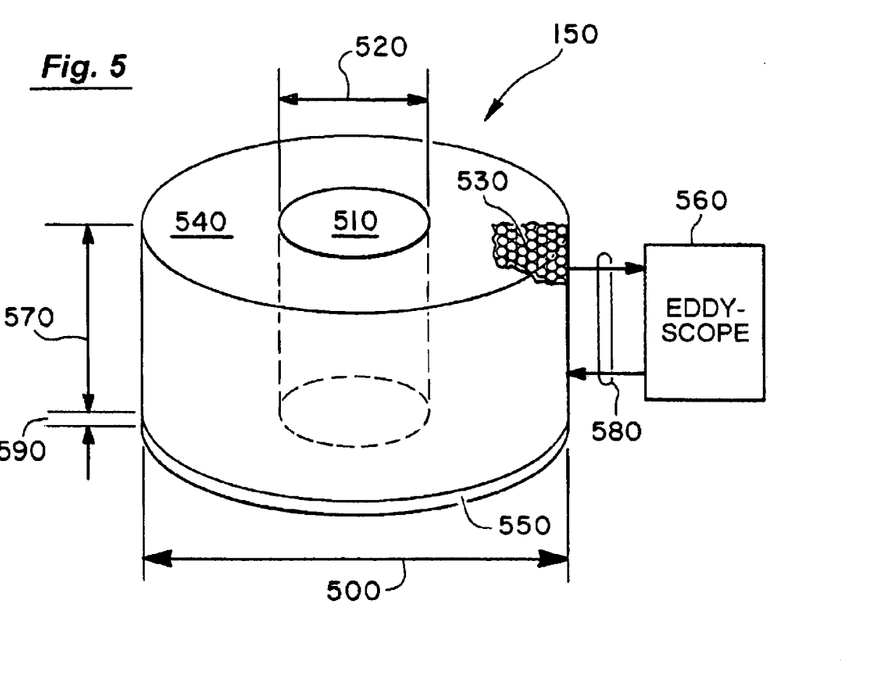
FIG. 5 is a perspective view of the low frequency eddy current probe of the present invention.

3. Low Frequency Eddy Current Probe. In FIG. 5, the details of the low frequency eddy current probe 150 are shown. In this embodiment, the diameter 500 of the coil 150 is 1⅛ inch. The core 510 is air and has a diameter 520 of ¼ inch. The height 570 of the coil is ¾ inch. The coil is made up of wire turns 530 which, in this embodiment, are 900 turns of 24 gauge enamel wire. The coil is immersed in epoxy resin 540 and has a protective TEFLON cap 550. The cap 550 has a thickness 590 of 50 mil.

In FIG. 5, the coil 150 of the present invention is shown. It is to be understood that a number of conventional eddy current probes are known including those set forth (i.e., pancake, ferrite-core cylindrical, ferrite pot-core probe, and gage side ferrite) in the aforesaid Earnest presentation which operates with varying degrees of sensitivity under the teachings of the present invention.

In one embodiment of the present invention, an eddyscope 560 provides power over lines 580 to the coil 150. In this embodiment, the coil 150 is driven at a low frequency such as 80 hertz. The gain of the eddyscope 560 is preferably set at 36.5. The probe 150 is a single coil which acts both as a sensor and an exciter. The eddyscope 560 monitors the impedance of the probe 150. This embodiment uses a Model MIZ-22 from Zetec Inc., 1370 N.W. Mall St., P.O. Box 140, Issaquah, Wash. 98027.

Figure 6:
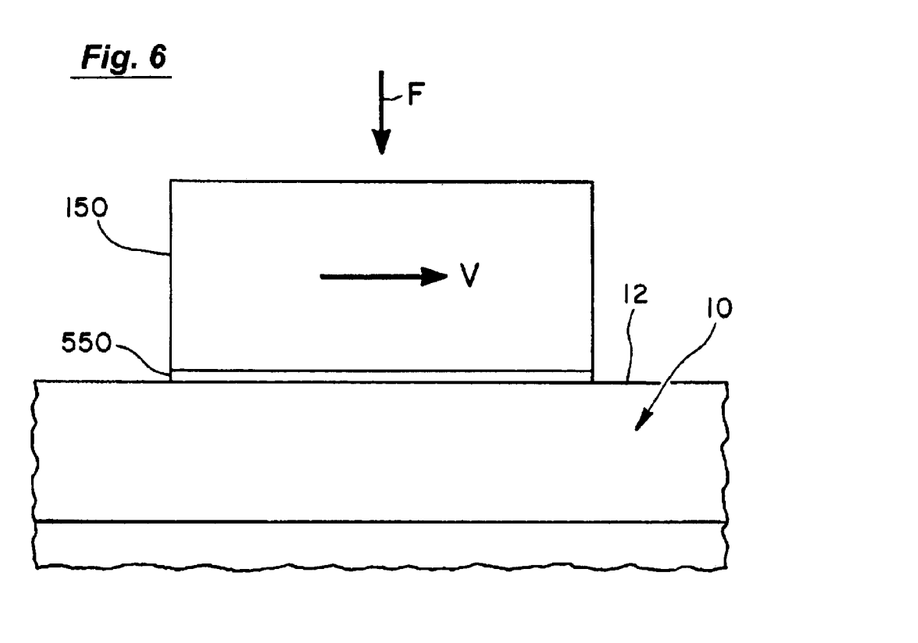
FIG. 6 is an illustration of the low frequency eddy current probe of FIG. 5 moving on the surface of the rail head.

As shown in FIG. 6, the cap 550 of the probe 150 abuts the surface 12 of the rail head 10 as the probe 150 moves with a velocity V. A force F is applied to the probe 150 to ensure contact of the probe cap 550 to the surface 12 especially to follow the wear pattern of the rail head 10.

Figure 7:
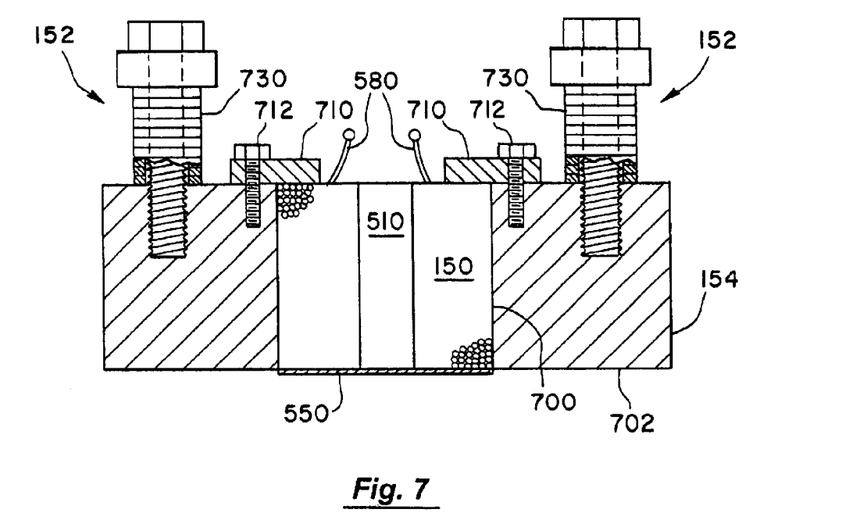
FIG. 7 is a cross section of the low frequency eddy current probe carriage of the present invention.

In FIG. 7, the probe 150 is mounted into a probe carriage 154. The probe 150 is set into a formed cavity 700 of the probe carriage 154 and is held in place by two brackets 710 which are bolted 712 to the carriage 154. This firmly holds the probe 150 in the carriage 154. The TEFLON cap 550 acts as a protective coating and extends slightly below the undersurface 702 of the carriage 154. The probe carriage 154 is mounted to the transporter 110 as shown in FIG. 2 in any of a number of conventional fashions. Springs 730 are provided about the mounting bolts 152 to provide the force F to engage the cap 550 with the upper surface 12 of the rail head 10. The force F causes the probe 150 to follow the wear profile of the rail surface 12 as the transporter moves. The force F also minimizes lift-off of the probe 150 from the rail surface 12.

Figure 10:
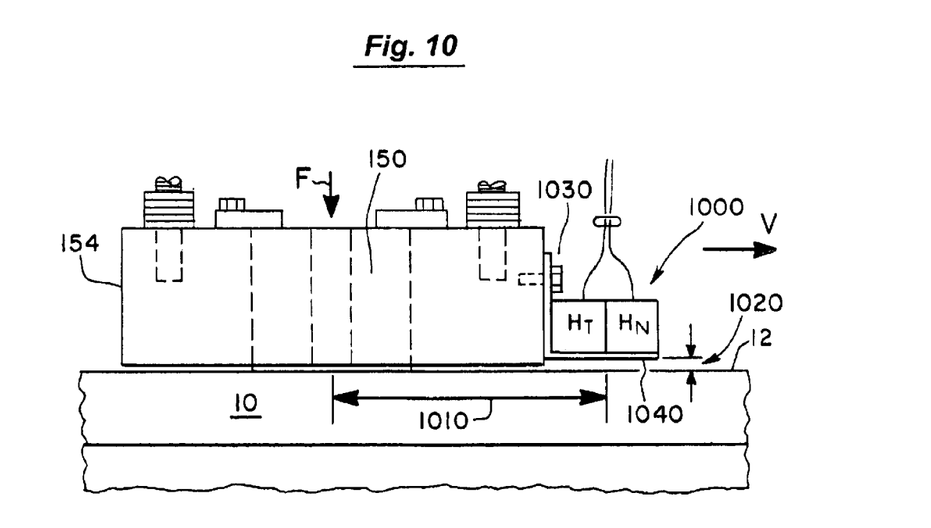
FIG. 10 is a side view of the carriage of FIG. 7 adapted, in an alternate embodiment, to carry all sensors.
Figure 14:
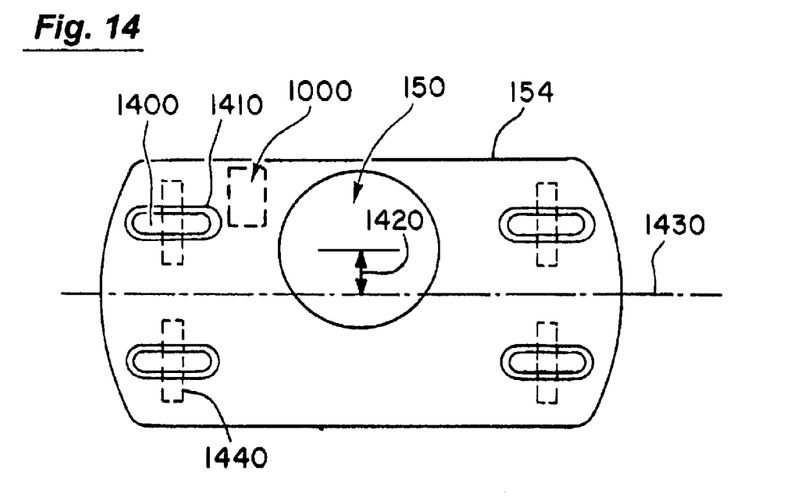
FIG. 14 is a bottom view of another embodiment of the probe carriage of the present invention.
Figure 15:
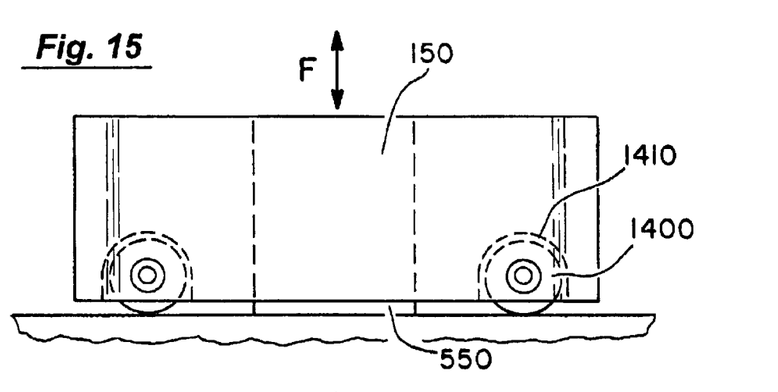
FIG. 15 is a side view of the probe carriage of FIG. 14.
Figure 16:
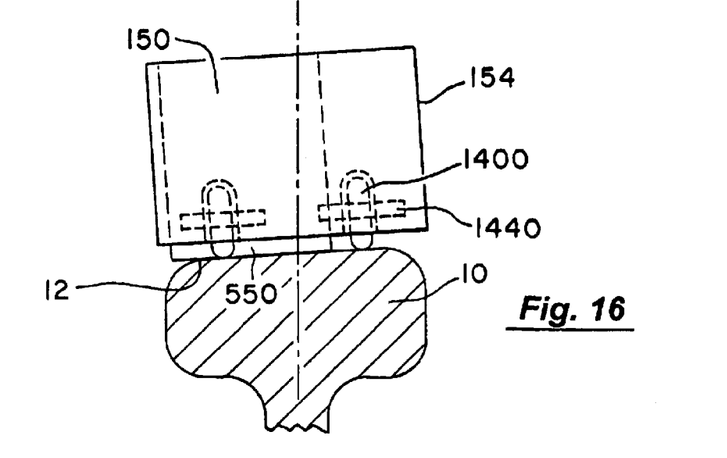
FIG. 16 is an end view of the probe carriage of FIG. 14.

In FIGS. 2, 7, and 10, a first embodiment of a carriage 154 is shown and in FIGS. 14, 15, and 16 a second embodiment is shown. The carriage 154 can be any structural means not limited to that shown, mounted to the transporter 110, for carrying the probe 150 centrally between the opposing pole ends 160 of the saturation magnet 140 and over the rail head 10 of rail 90. For example, the shape of the carrying means could be entirely curved rather than linear or a combination of both linear and curved. For example, the carrying means could be solid, as shown, hollow, or similar to a basket or bracket design. The shape or design can be any suitable configuration to structurally support the probe between the pole ends 160 over the rail head 10 as the transporter 100 moves along the rail.

In FIGS. 7 and 10, springs 730 are used to provide force F to probe 150. While this is one embodiment any conventional means for applying the force F can be used. For example, any type of springs such as leaf springs could be used and any number of springs could be used such as 1, 3, or 4 or more. The force F could be other than a spring such as a pressurized gas force or a pneumatic force. Any structural means can be utilized under the teachings of this invention to apply the force F to the carriage 154 or, in a variation, directly to the probe 150.

The probe carriage 154 is constructed of aluminum so as not to affect the flux path of the saturation magnet 140 nor to affect the eddy current in the probe 150.

Figure 8:
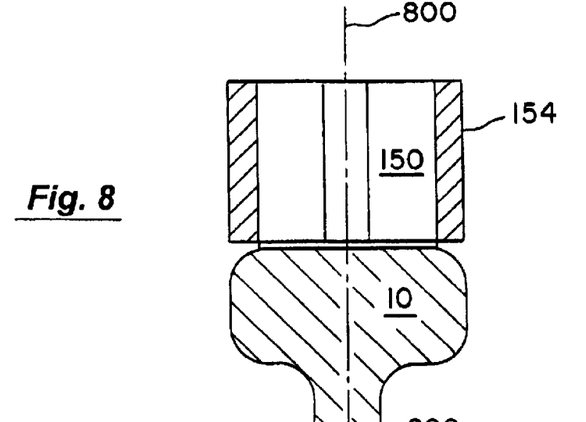
FIG. 8 shows the low frequency eddy current probe carriage of FIG. 7 on a rail head.
Figure 9A:
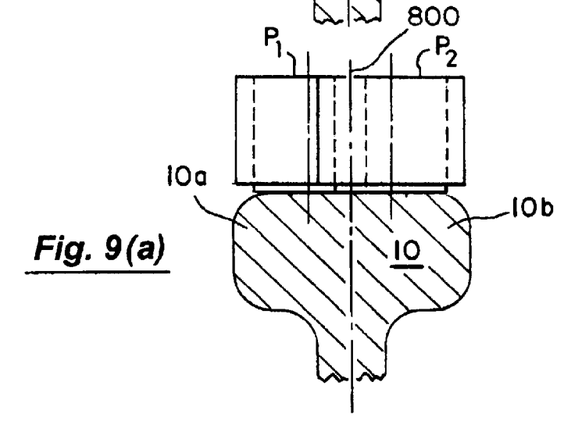
FIGS. 9a and 9b set forth an alternate embodiment of the present invention wherein two probes are used on the rail head.
Figure 9B:
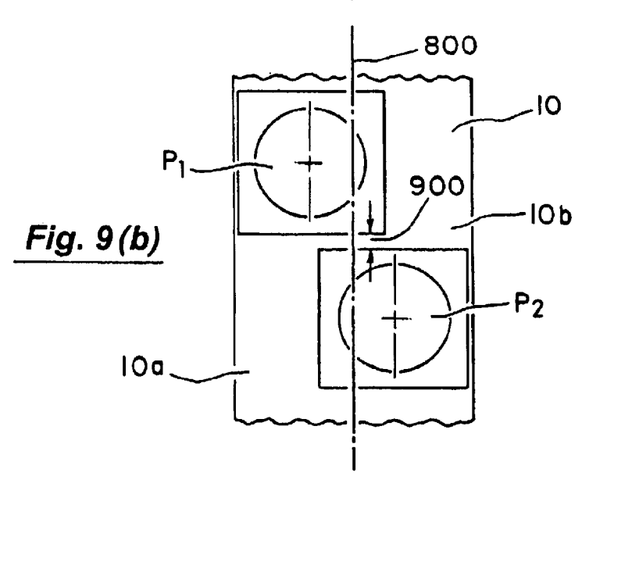

In FIG. 8, the carriage 154 is located over the centerline 800 of the rail head 10 thereby centering the probe 150. In another embodiment, two probes could be utilized such as probes P1 and P2 in FIG. 9. In FIG. 9(a), the two probes are offset from the center 800 of the rail head 10 so as to concentrate their detection at the opposing sides 10a and 10b of the rail head 10. Probes P1 and P2 are offset by a predetermined distance 900 as shown in FIG. 9(b) but overlap to provide full coverage of the rail head.

In FIGS. 14–16 and in another embodiment of the present invention, the probe carriage 154 is shown to have a plurality of wheels 1400 which ride on the surface 12 of the rail head 10. In this embodiment, the probe 150 is located off the centerline 1430 by a distance 1420. As shown in FIG. 16, this positions the probe 150 over to one side of the rail head 10. The use of the wheels 1400 allow the carriage 154 to follow the surface 12 under the bias force F while minimizing lift-off of the probe 150 from the surface 12. This is especially true when the rail head 10 is worn as shown in FIG. 16. In which case, the wheels actually follow along on the wear profile of the surface 12 of the rail head 10. Yet, the TEFLON cap 550 slideably engages along the surface 12.

As shown in FIG. 14, four wheels 1400 are each mounted in a wheel well 1410 on an axle 1440. It is to be expressly understood that while wheels are utilized, any suitable support means for controlling lift-off could be used under the teachings of the present invention. For example, such supports rather than being rolling wheels could be TEFLON pads. Any suitable support means for controlling lift-off and/or following the wear profile surface can be utilized under the teachings of the present invention. The use of wheels 1400 can occur with the embodiment shown in FIG. 7. The present invention includes a number of variations concerning the force F, the carriage 154, the probe 150, the supports 1400 and the protective cap 550. In one embodiment, the force F pushes the cap 550 in the carriage 154 against the rail surface 12. In this embodiment, supports 1400 (e.g., wheels) can also be used or not be used. In a second embodiment, the force F pushes the carriage 154 with supports 1400 towards the rail surface 12, but the cap 550 does not contact the rail surface. In which case, the supports 1400 engage the rail surface 12. In this embodiment, the cap 550 may or may not be used.

4. Separate Sensor. In FIG. 10, the carriage 154 has separate sensors 1000 such as Hall element sensors mounted a predetermined distance 1010 to the low frequency eddy current probe 150. The Hall sensors 1000 are two perpendicular Hall sensors $H_T$(tangential) and HN(normal). The Hall element sensors 1000 are spaced above the surface 12 of the rail head 10 by an amount shown as 1020 which is typically around 1 mil. The Hall element sensors 1000 are mounted 1030 to the carriage 154 so as to take advantage of the force F as previously discussed (and/or in another embodiment the supports 1440). How the Hall element sensors 1000 are physically mounted to the carriage is immaterial to the teachings of the present invention and a variety of conventional approaches could be utilized for providing this mount. Furthermore, while one variation has the Hall element sensors 1000 mounted to the carriage 154 near the probe 150, in other variations of the present invention, the Hall element sensors are mounted in different relationships to the probe 150 either on the carriage 154, within the carriage 154 (as shown by dotted lines 1000a) or at other locations on the transporter 110. In the shown embodiment of FIG. 10, the sensors 1000 are located near the probe 150 and separated by a known distance 1010.

The Hall element sensors 1000 provide added signal information which helps classify the low frequency eddy current signals produced by the probe 150. In particular, the Hall sensors 100 have been included to detect a voltage perpendicular to the direction of current (from the saturating magnet). When a change in the magnetic field occurs a change in the polarity also occurs allowing the Hall voltage to measure magnetic flux density changes between thermite welds, plant (electric flash butt) welds, and rail end joints, to that of the parent rail material. These are termed "non-relevant indications." Use of the Hall element sensors 1000 supplements the eddy current signals for classification of rail head conditions.

The Hall sensors 1000 are commercially available such as those available from Bell Technologies Inc., a SYPRIS Company, 6120 Hanging Moss Road, Orlando, Fla. 32807 (800)775–2550.)

It is to be expressly understood that in one variation of the present invention more than one set of Hall sensors 1000 could be used near the probe 150.

While one embodiment of the present invention uses Hall sensors, it is to be expressly understood that any other separate sensor(s) could be utilized in conjunction with the low frequency eddy current probe 150 to generate signals that classify the signals generated by the low frequency eddy current probe. Any type of secondary (and, perhaps tertiary) sensor or group of sensors can be used in conjunction with the system 100 of the present invention to aid in the classification of data obtained by the eddyscope.

Figure 11:
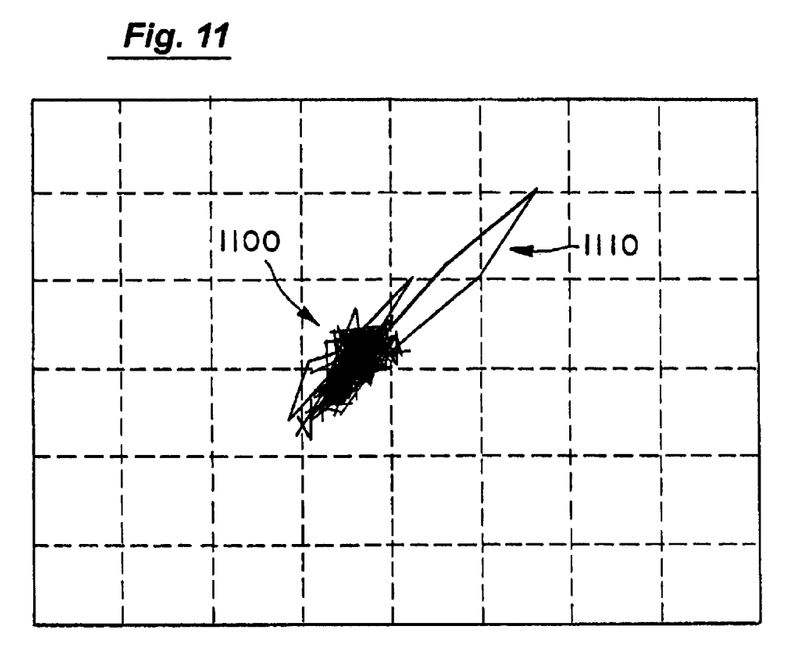
FIG. 11 is an output screen of the eddyscope showing a transverse crack detection signal.

5. Signal Analysis. In FIG. 11, a typical low frequency eddy current signal from the eddyscope 560 is shown. The received eddy current signal from the probe 150 is shown as signal 1100 and the flaw signal corresponding to a transverse crack 50 is shown as signal 1110. Signals 1100 and 1110 show changes in the inductance of the probe 150 over lines 580 as sensed by the eddyscope 560. Signal 1110 represents the possible detection of a transverse crack. The eddyscope screen shows a phase vector or phasor diagram comparing amplitude and phase relationship of current signals at a set frequency. The Y-axis is inductive reactance and the X-axis represents resistance.

Figures 12A, 12B:
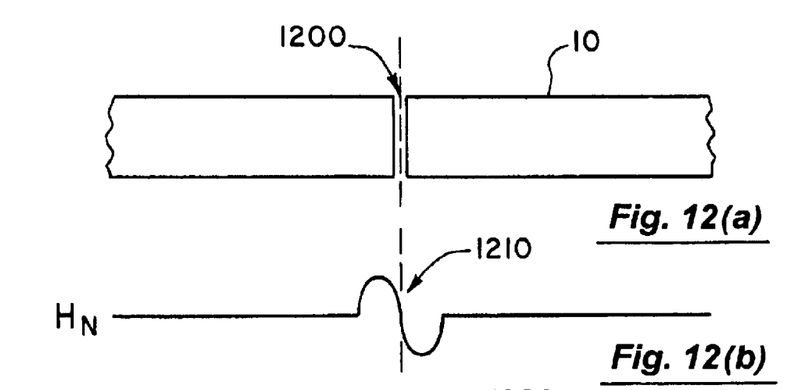
FIGS. 12a, 12b, and 12c show the output signals from the Hall sensors for a joint in the rail head.
Figure 12C:
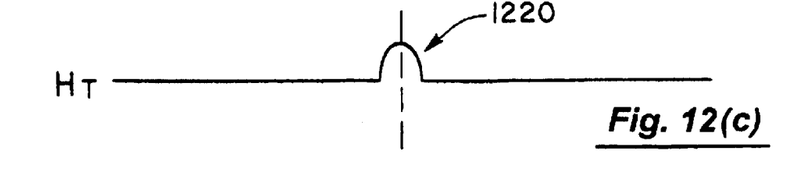

In FIG. 12, the operation of the separate Hall sensors 1000 is shown. When a non-relevant indication 1200 appears in the rail head 10, the first Flail sensor $H_N$ delivers a wave form 1210 and the second Hall sensor $H_T$ delivers a wave form 1220. The presence of these signals would cause the system 10 of the present invention, as will be explained later, to classify the corresponding transverse crack signal 1110 as shown in FIG. 11.

Figure 13:
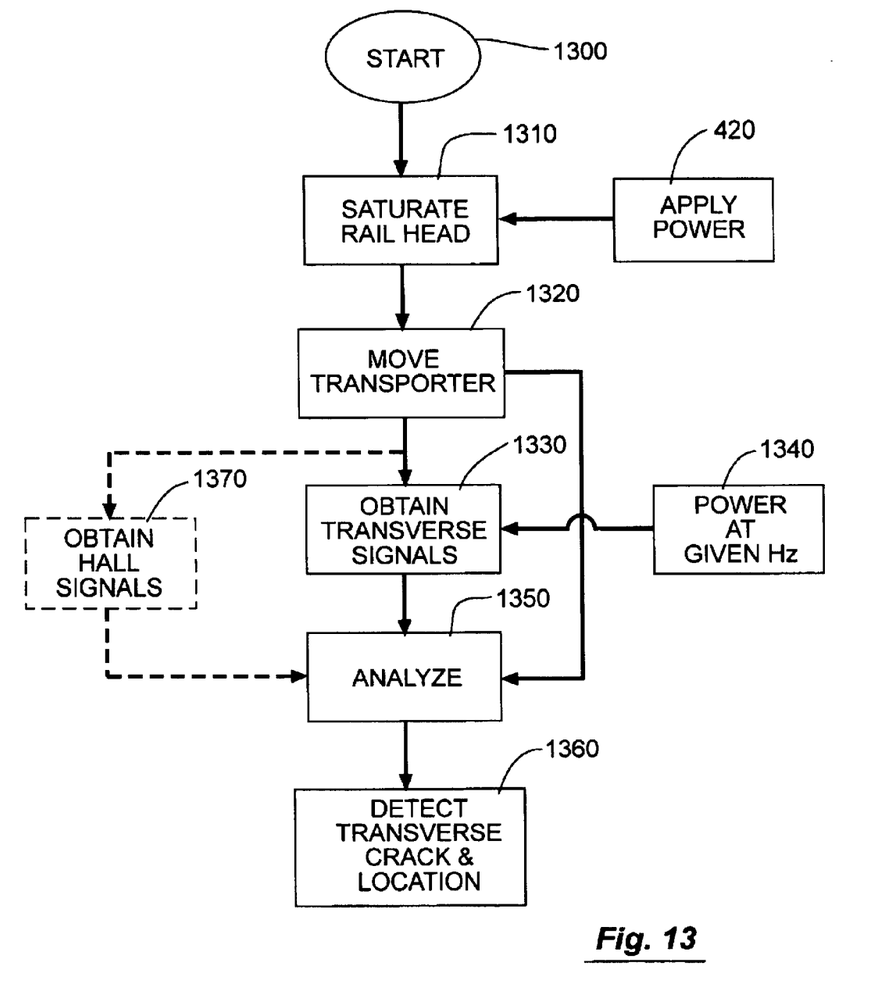
FIG. 13 is a flow chart showing the operation of the low frequency eddy current probe of the present invention.

6. Operation. In FIG. 13, the operation of the present invention is shown and starts in step 1300. The process saturates 1310 the rail head 10 with the DC saturation magnet 140. The DC saturation magnet 140 is powered by power supply 420. The transporter 110 moves 1320 forward at a given velocity V and, during this movement the low frequency eddy current probe 150 and eddyscope 560, obtains 1330 transverse crack defect signals. The probe 150 is powered 1340 at a given frequency. These signals are then analyzed 1350. Once analyzed, the results are formulated and delivered 1360 which shows the detection, approximate size, and location of the transverse crack on the track. A number of conventional software packages are available for analyzing signals from eddy current instruments. First, the signal to noise ratio can be conventionally processed through averaging or other standard signal processing techniques. The improved signal can then be further processed through conventional neural network software, etc.

In an alternate embodiment, the separate sensor signals (e.g., from Hall sensors) are obtained in stage 1370. As shown in FIGS. 11 and 12, when the probe 150 passes over a non-relevant indication 1200 the resulting signal 1110 in the eddyscope appears to sense a transverse crack 50. But, the Hall sensors 1000 issue signals 1210 and 1220 when they pass over the non-relevant indication 1200. The occurrence of signals 1210 and 1220 classify the corresponding signal 1110 as one corresponding to a non-relevant indication 1200 and, hence, stage 1350 ignores or rejects signal 1110. In a variation to the present invention, this can be classified as a non-relevant indication in stage 1360. For all other signals 1110 when corresponding Hall signals 1210 and 1220 do not exist, they are classified as transverse cracks 50 in stage 1350 and outputted in stage 1360.

It is well known how to use velocity, V, GPS readings, etc. to physically locate actual defects on track in stage 1360 based on locating hardware, algorithms and software.

We claim:

1. A system for detecting transverse cracks in rail head on railway track comprising:
   a transporter on the railway track, said transporter moving the system along the railway track,
   a toroidal-shaped DC magnet mounted to the transporter with its opposing pole ends inwardly directed towards each other and aligned over the rail head,
   an inductive coupling between each of the poles and the rail head to magnetically saturate the rail head, the inductive coupling slideably engaging the rail head,
   at least one low frequency eddy current probe, centrally located between the poles of the toroidal-shaped DC magnet, for sensing said transverse cracks in the rail head,
   protective material on the low frequency eddy current probe,
   a carriage mounted to the transporter forcing said low frequency eddy current probe against said rail head, the protective material abutting the rail head when the transporter moves on the railway track thereby protecting the low frequency eddy current probe from damage.

2. The system of claim 1 further comprising:
   one of a plurality of supports on said carriage engaging the rail head for controlling lift-off of the low frequency eddy current probe from the rail head.

3. The system of claim 2 wherein said plurality of supports are wheels.

4. The system of claim 1 wherein the toroidal-shaped DC magnet has four layers of windings extending down towards the opposing ends.

5. The system of claim 1 wherein the inductive coupling comprises a plurality of carbon steel bristles mounted to each of the pole ends.

6. The system of claim 1 wherein the low frequency eddy current probe is an air core coil.

7. The system of claim 1 wherein the protective material is polytetrafluoroethylene.

8. The system of claim 1 wherein the carriage comprises two spring-loaded supports.

9. The system of claim 1 wherein the plurality of wheels is four.

10. The system of claim 1 wherein the carriage locates the low frequency eddy current probe off the center of the rail.

11. The system of claim 1 wherein the at least one probe is one probe, the aforesaid one probe centered over the centerline of the rail head.

12. The system of claim 1 wherein the at least one probe is a plurality of probes, each of the aforesaid plurality of probes located across the rail head.

13. A system for detecting transverse cracks in rail head on railway track comprising:

a transporter on the railway track, said transporter moving the system along the railway track, a toroidal-shaped DC magnet mounted to the transporter with its opposing pole ends inwardly directed towards each other and aligned over the rail head, an inductive coupling between each of the poles and the rail head to magnetically saturate the rail head, the inductive coupling slideably engaging the rail head, at least one low frequency eddy current probe, centrally located between the poles of the toroidal-shaped DC magnet, for sensing said transverse cracks in the rail head, protective material on the low frequency eddy current probe, a separate sensor near said low frequency eddy current probe for sensing non-relevant indications in the rail head, said separate sensor held a predetermined distance above said rail head, said system rejecting a sensed transverse crack when the separate sensor senses a non-relevant indication, a carnage mounted to the transporter forcing said low frequency eddy current probe against said rail head, the protective material abutting the rail head when the transporter moves on the railway track thereby protecting the low frequency eddy current probe from damage.

14. The system of claim 13 wherein the separate sensor is a Hall element sensor.

15. A system for detecting transverse cracks in rail head on railway track comprising:

a transporter on the railway track, said transporter moving the system along the railway track, a DC magnet mounted to the transporter with its opposing pole ends aligned over the rail head, an inductive coupling between each of the poles and the rail head to magnetically saturate the rail head, the inductive coupling slideably engaging the rail head, at least one low frequency eddy current probe, centrally located between the poles of the DC magnet and over said rail head, for sensing said transverse cracks in the rail head, a separate sensor near said low frequency eddy current probe for sensing non-relevant indications in the rail head, said separate sensor held a predetermined distance above said rail head, said system rejecting a sensed transverse crack from the low frequency eddy current probe in an area of the rail head when the separate sensor senses a non-relevant indication at said area.

16. A method for detecting transverse cracks in rail head of a rail comprising:

moving a transporter on the rail, generating a saturated magnetic field into and across the rail head with a DC saturation magnet mounted to the transporter a predetermined distance above the rail head while the transporter is moving, the saturation magnet having a toroidal-shape with opposing pole ends inwardly directed towards each other over the rail head, inductively coupling the opposing pole ends of the DC saturation magnet with the rail head, detecting transverse cracks in the rail head with a low frequency eddy current probe mounted centrally between the opposing pole ends of the DC saturation magnetic and over the rail head, applying a force to the low frequency eddy current probe against the rail head as the transporter moves on the rail, controlling lift-off of the low frequency eddy current probe from the rail head as the transporter moves on the rail.

17. A method for detecting transverse cracks in rail head of a rail comprising:

moving a transporter on the rail, generating a saturated magnetic field into and across the rail head with a DC saturation magnet mounted to the transporter a predetermined distance above the rail head while the transporter is moving, the saturation magnet having a toroidal-shape with opposing pole ends inwardly directed towards each other over the rail head, inductively coupling the opposing pole ends of the DC saturation magnet with the rail head, detecting transverse cracks in the rail head with a low frequency eddy current probe mounted centrally between the opposing pole ends of the DC saturation magnetic and over the rail head, applying a force to the low frequency eddy current probe against the rail head as the transporter moves on the rail, controlling lift-off of the low frequency eddy current probe from the rail head as the transporter moves on the rail, sensing non-relevant indications in the rail head with at least one separate sensor, rejecting a detected transverse crack by the low frequency eddy current probe when it corresponds to a sensed non-relevant indication by the at least one separate sensor.

18. A method for detecting a transverse crack in rail head of a rail comprising:

moving a transporter on the rail, generating a saturation magnetic field into and across the rail head with a DC saturation magnet mounted to the transporter a predetermined distance above the rail head while the transporter is moving, inductively coupling the opposing pole ends of the DC saturation magnet with the rail head, detecting a possible transverse crack in an area of the rail head with a low frequency eddy current probe mounted centrally between the opposing pole ends of the DC saturation magnetic and over said area of the rail head, sensing a non-relevant indication in said area of the rail head with at least one separate sensor, rejecting said possible detected transverse crack by the low frequency eddy current probe only when said a non-relevant indication is sensed by the at least one separate sensor for said area.

* * * * *